US009322815B2

(12) United States Patent
Srinivasan et al.

(10) Patent No.: US 9,322,815 B2
(45) Date of Patent: Apr. 26, 2016

(54) ION CHROMATOGRAPHY SYSTEM WITH ELUENT RECYCLE

(75) Inventors: Kannan Srinivasan, Tracy, CA (US); Rong Lin, Sunnyvale, CA (US); Sheetal Bhardwaj, Fremont, CA (US); Christopher A. Pohl, Union City, CA (US)

(73) Assignee: DIONEX CORPORATION, Sunnyvale, CA (US)

(*) Notice: Subject to any disclaimer, the term of this patent is extended or adjusted under 35 U.S.C. 154(b) by 399 days.

(21) Appl. No.: 12/036,544

(22) Filed: Feb. 25, 2008

(65) Prior Publication Data

US 2009/0211979 A1    Aug. 27, 2009

(51) Int. Cl.
G01N 30/96    (2006.01)

(52) U.S. Cl.
CPC ....................................... G01N 30/96 (2013.01)

(58) Field of Classification Search
CPC ............................... G01N 30/26; G01N 30/96
USPC .............. 210/198.2, 635, 638, 656, 659, 748, 210/243; 205/789, 792
See application file for complete search history.

(56) References Cited

U.S. PATENT DOCUMENTS

| | | | |
|---|---|---|---|
| 4,272,246 A | 6/1981 | Fritz et al. | |
| 4,732,686 A | 3/1988 | Small et al. | |
| 5,045,204 A | 9/1991 | Dasgupta et al. | |
| 5,597,734 A | 1/1997 | Small et al. | |
| 5,773,615 A | 6/1998 | Small et al. | |
| 6,036,921 A | 3/2000 | Small et al. | |
| 6,093,327 A | 7/2000 | Anderson, Jr. et al. | |
| 6,225,129 B1 | 5/2001 | Liu et al. | |
| 6,315,954 B1 | 11/2001 | Small et al. | |
| 6,316,270 B1 | 11/2001 | Small et al. | |
| 6,316,271 B1 | 11/2001 | Small et al. | |
| 7,329,346 B2 | 2/2008 | Liu et al. | |
| 2003/0127392 A1 | 7/2003 | Srinivasan et al. | |
| 2006/0186046 A1 | 8/2006 | Liu et al. | |

FOREIGN PATENT DOCUMENTS

| | | |
|---|---|---|
| JP | 2008531992 A | 8/2008 |
| WO | WO 96 27793 A1 | 9/1996 |
| WO | WO 98 32011 A1 | 7/1998 |
| WO | 2006091404 A2 | 8/2006 |
| WO | WO 2006 091404 A2 | 8/2006 |

OTHER PUBLICATIONS

Yokoyama et al. Anion chromatography using on-line recycled eluents. *J. Chromatogr. A* 1089:82-86 (2005).
Fritz, J.S. Early milestones in the development of ion-exchange chromatography: a personal account. *Journal of Chromatography A*, 1039:3-12 (2004).
Twohill, E. and B. Paull. Zwitterionic ion chromatography using a dynamically coated column and mobile phase recycling. *Journal of Chromatography A*, 973(1-2):103-113 (2002).

*Primary Examiner* — Ernest G Therkorn
(74) *Attorney, Agent, or Firm* — David J. Brezner

(57) ABSTRACT

Ion chromatography apparatus including (a) a chromatographic column, (b) a source of an aqueous eluent liquid stream, (c) a detector, (d) a recycle line between the detector and the chromatographic column, and (e) a purifying device disposed along the recycle line including ion exchange removal medium. Also, such apparatus with an electrolytic purifying device disposed along the recycle line. Also, methods of using such apparatus.

4 Claims, 4 Drawing Sheets

ION CHROMATOGRAPHY SYSTEM WITH ELUENT RECYCLE

BACKGROUND OF THE INVENTION

Single column ion chromatography, termed "SCIC" herein, encompasses ion chromatography applications that do not use a suppressor. In the early days of ion chromatography a packed bed suppressor led to several potential problems such as added delay volume causing band broadening, a dependence of the signal on the degree of exhaustion of the packed bed, a need to frequently regenerate the bed, and the like. Therefore, some investigators investigated methods of ion chromatography without the suppressor. See U.S. Pat. Nos. 4,272,246 and 4,732,686.

Eluent or mobile phase recycle in HPLC is predominantly pursued in the isocratic mode by collecting fractions during the analysis and targeting regions in the chromatogram where there are no peaks. Typically a valve is switched to divert the analyte peaks to waste while collecting the mobile phase during the baseline portion of the chromatogram and diverting it back to the mobile phase reservoir. While this approach is commonly used, it suffers from several limitations such as (a) the approach is only feasible when the analyte levels are significantly higher than the baseline noise, (b) since the method relies on distinguishing the baseline portion from the peaks of interest and when the analyte levels are close to the minimum detection limits the differences become small and it is difficult to cleanly fractionate the solvent portion, and (c) the method works well when the number of peaks in the chromatogram are low since it relies on the availability of regions that do not contain the analytes. There are several commercial modules that are available for the solvent recycling such as a module called S3-Solvent Recycler from Spectrum Corporation, Houston, Tex., USA.

Early workers also directly recycled the mobile phase after separation by diverting the waste liquid back into the mobile phase reservoir. Since the analytes are also recycled in this approach along with eluents only limited amount of recycle was possible. Additionally when the analyte ions were present at significant concentrations they affected the separation and the background.

An ion chromatography approach to recycle was investigated by Yokoyama et. al (*J. Chromagr. A* 1089, (2005), 82-86. In this approach an aliquot of mixed bed resin was added to the eluent reservoir and stirred. When a packed column embodiment with the mixed bed resin was used in the above setup poor analyte removal was observed and the baseline drifted upwards. The analyte ions were eluted off the mixed bed ion exchange column by the eluent. Adding the mixed bed resin to the eluent reservoir however yielded improved performance as evident from being able to operate with 5× lower eluent volume. The approach however relied on equilibration of the resin with the analyte ions for removal, and a stirrer was needed to ensure good contact of the resin with the analyte ions dissolved in the eluent.

There is a need for an improved SCIC system.

SUMMARY OF THE INVENTION

In one embodiment, ion chromatography apparatus is provided including (a) a chromatographic column comprising ion exchange separation medium having exchangeable ions of one charge, positive or negative, for separating analyte ions of the same charge as the exchangeable ions, and having an inlet and an outlet, the chromatographic column not being associated with electrodes for passing an electric current through the separation medium, (b) a source of an aqueous eluent liquid stream in fluid communication with the chromatographic column inlet, (c) a detector for detecting analyte ions in a sample downstream from the chromatographic column outlet and in fluid communication therewith, (d) a recycle line providing fluid communication between the detector and the chromatographic column inlet, and (e) a purifying device disposed along the recycle line including ion exchange removal medium with exchangeable ions of the same charge as the separation medium exchangeable ions, the apparatus not including a suppressor disposed between the chromatographic column outlet and the detector.

In another embodiment, ion chromatography apparatus is provided including (a) a chromatographic column including ion exchange separation medium having exchangeable ions of one charge, positive or negative, for separating analyte ions of the same charge as the exchangeable ions, and having an inlet and an outlet, (b) a source of an aqueous eluent liquid stream in fluid communication with the chromatographic column inlet, (c) a detector for detecting the analyte ions downstream from the chromatographic column outlet and in fluid communication therewith, (d) a recycle line providing fluid communication between the detector and the chromatographic column inlet, and (e) an electrolytic purifying device disposed along the recycle line and including ion exchange removal medium with exchangeable ions of the same charge as the exchangeable ions, and a pair of electrodes disposed to apply an electric field across the ion exchange removal medium to continuously regenerate the ion exchange removal medium.

In another embodiment, an ion chromatography method is provided including (a) flowing sample analyte ions of one charge, positive or negative, in an aqueous eluent solution to a chromatographic column including ion exchange medium having exchangeable ions of the same charge as the analyte ions, (b) chromatographically separating the analyte ions in the chromatographic column under non-electrolytic conditions, (c) detecting the separated analyte ions, the method being performed in the absence of suppression of the eluent ions between the separating and detection steps, (d) recycling the detected sample solution and eluent solution from the detector to the chromatographic column, and (e) during the recycle step, flowing the detected sample solution through a purifying device including ion exchange removal medium to remove the analyte ions prior to flow into the chromatographic column.

In another embodiment, an ion chromatography method is provided including (a) flowing analyte ions of one charge, positive or negative, in an aqueous eluent stream to a chromatographic column including ion exchange medium having exchangeable ions of the same charge as the analyte ions, (b) chromatographically separating the analyte ions in the chromatographic column, (c) detecting the separated analyte ions, (d) recycling the detected sample solution and aqueous eluent stream from the detector to the chromatographic column, and (e) during the recycle step, flowing the detected sample solution through an electrolytic purifying device including ion exchange removal medium and a pair of electrodes and applying an electric current across the ion exchange removal medium to remove the analyte ions from the solution prior to flow into the chromatographic column.

DETAILED DESCRIPTION OF PREFERRED EMBODIMENTS

One embodiment of the present invention relates to eluent recycle in an SCIC system. During SCIC anion analysis, a sample containing both anions and cations typically is injected into a low capacity chromatography column and eluted with an appropriate eluent. The sample anions of interest are retained in the chromatography column while an equivalent amount of eluent anions along with unretained sample counter ions are released from the chromatography column. During analysis, this results in a peak at the beginning of a chromatogram. This peak could be positive if the sum of the conductance of the anions and the cations in the sample plug is greater than that of the equivalent conductance of the eluent or a negative peak is detected. Similarly, the analyte anions of interest after separation when eluted off the chromatography column have occupied an equivalent concentration of the eluent thereby upon detection with conductivity detection would give a positive peak if the equivalent conductance of the analyte anion and eluent counter ion is higher than the equivalent conductance of the eluent or will give a negative peak.

Typical eluents used in SCIC analysis for anions contain an aromatic organic anion that has a high selectivity for the stationary phase. It is preferable to choose an eluent anion that has a higher affinity for the stationary anion exchange phase than the analyte anion. This allows elution of the sample anions using lower concentration of eluent, thus leading to a lower total conductivity background and lower peak to peak noise, and thus overall enhancing the signal to noise ratio.

For SCIC, in order to ensure the equivalent conductance contribution from the eluent is low the eluent pH typically is adjusted roughly between 4 and 7. A sodium hydroxide eluent may also be used. The anion analyte peaks would be negative since typically the equivalent conductance of the eluent exceeds that of the typical sample plug. Alternatively, a combination of sodium hydroxide and an aromatic anion such as benzoate may be used. This combination may allow faster elutions on some columns. An advantage of the use of basic eluents is the ability to dissociate very weak acids such as borate and silicate and thus allow sensitive detection with conductivity detection. Another benefit of SCIC is the analytes are detected in the salt form hence providing a linear response with increasing concentration for weakly dissociated species. In contrast, suppressed chromatography weakly dissociated species typically provide a quadratic response with increasing concentration.

Figure 1:
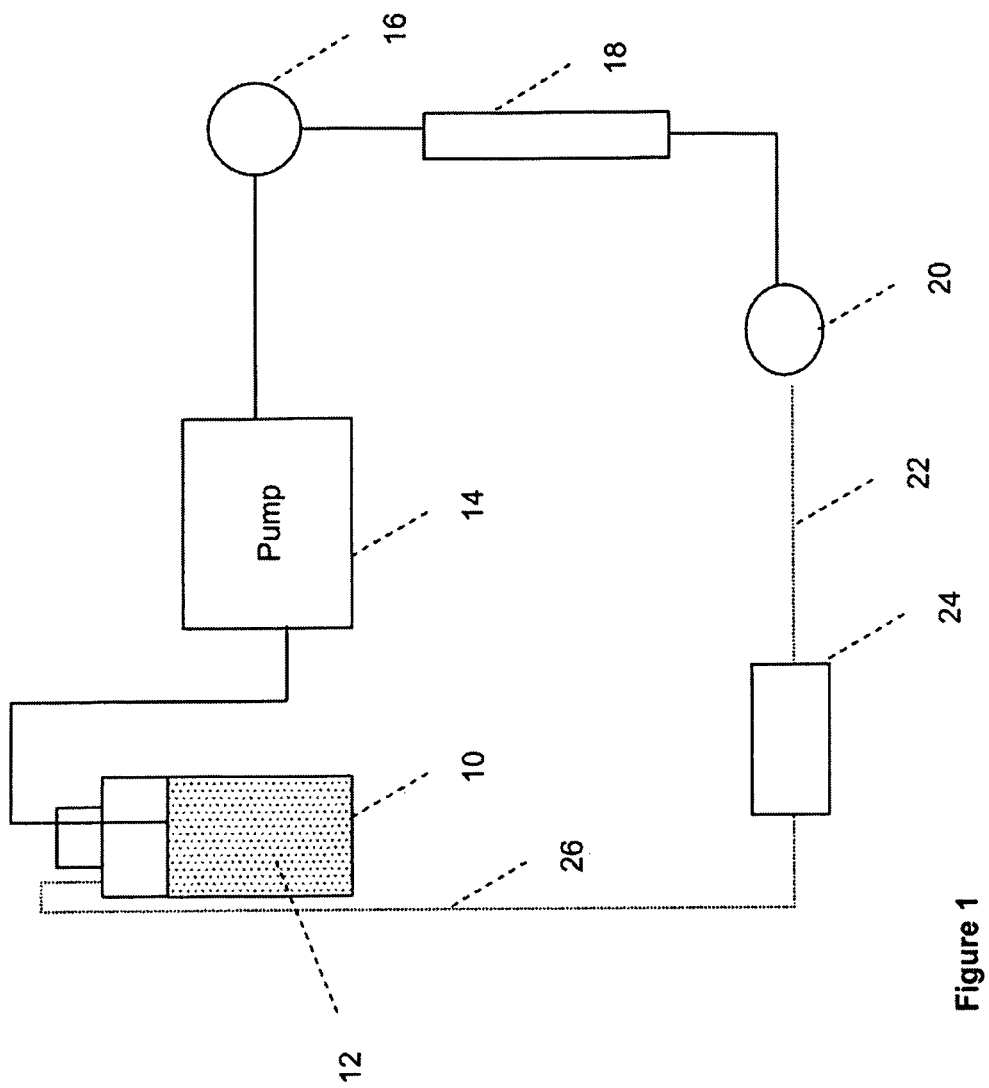
FIGS. 1 and 2 are schematic representations of single column ion chromatography systems according to the invention.

FIG. 1 depicts one embodiment of an SCIC recycle system of the present invention. In operation, an aqueous eluent solution 12 is pumped from reservoir 10 using pump 14 and is routed to injection valve 16 and then to separation medium, typically ion exchange resin in a chromatography column 18. This portion of the SCIC setup is similar to a standard ion chromatography setup such as illustrated in U.S. Pat. No. 7,329,346, incorporated herein by reference. As used herein, the terms "eluent solution" or "aqueous eluent" encompass an aqueous solution with no substantial electrolyte, i.e. with insufficient electrolyte to be used as a developing reagent in chromatography, as well as a conventional chromatography eluent solution which includes an electrolyte, e.g. an acid, base, or salt, used as a developing reagent to release sample ions retained on a chromatography column.

The effluent from column 18 is directed to a flow-through cell 20 of a detector (preferably a conductivity detector cell) via conduit 22 and then to a purifier device 24. Other detectors used in the chromatography field may also be used. Solution exiting the outlet of purifier device 24 is recycled back to the reservoir 10 via conduit 26.

Purifier device 24 includes ion exchange removal medium. In one embodiment the medium is flow-through ion exchange material, such as a packed bed of ion exchange resin or a flow-through ion exchange monolith in a flow-through housing such as a column. Here, device 24 is packed with appropriate ion exchange medium that removes the analytes of interest. Thus, the recycle line returns eluent without substantial sample analyte ions to reservoir 10. In one embodiment, the eluent includes an electrolyte, e.g. a base for analysis of anions. The base is unaffected by the purifying device, and it recycles to the reservoir. When using an eluent with electrolyte, chromatographic separation can be performed in a chromatographic column unassociated with electrodes for passing an electric current through the separation medium.

The recycle stream to reservoir 10 includes sample counter ions. For the electrolyte containing eluent embodiment, the total background conductivity is high due to the relatively high concentration of electrolyte. Thus, the relatively low sample counter ion concentration has a minimal affect on the overall performance of the SCIC system.

In another embodiment, the analyte counter ions may be removed in addition to the analyte ions. This may be accomplished by use of a mixture of cation and anion exchange resin in purifier device 24 or by the use of a second purifier device with resin of opposite charge. Thus, these purification tasks can be performed in one column or via multiple columns by using appropriate resins. For example a high capacity anion exchanger in the eluent ion form could be used to remove the anion analytes of interest. Similarly, the sample cations can be removed and replaced with either hydronium or to the eluent cation form. Commercial packed beds of ion exchange resin sold by Dionex Corporation called cation polisher column CP1 and CP2 could be used for this purpose. Such columns are described as eluent purifier column in U.S. Pat. No. 7,329,346.

A key objective is to return a purified eluent back to the eluent reservoir free of analyte ions for further usage as an eluent. It is preferable to regenerate the ion exchange removal medium when the column capacity is depleted. Regeneration could be performed in a batch mode or in a frequent basis or could be automated by using multiple columns that would be switched inline and regenerated one at a time. Such switching practices are well known in the prior art for operation of suppressors, e.g. in U.S. Pat. No. 5,597,734, incorporated herein by reference. Known packed bed suppressor regeneration technologies are applicable to regeneration of the purifier ion removal medium. The ion exchange removal medium of such purifying devices could be flow-through ion exchange monolith in place of the packed bed of ion exchange resin.

In another embodiment, not shown, the chromatographic column of FIG. 1 includes a pair of spaced electrodes for passing current through ion exchange separation medium. Electrolytic regeneration systems for a packed bed suppressor are illustrated in U.S. Pat. Nos. 5,773,615 and 6,093,327, incorporated herein by reference. Here, the aqueous eluent solution may be electrolyte-free or one including electrolyte developing reagent may be used. In this embodiment the separation occurs in the ion exchange separation medium and the separated components are routed through a detector cell. At this point the analyte is in an aqueous eluent solution that may be electrolyte-free or including an electrolyte. The aqueous eluent solution is routed back to the reservoir. A purifying device of the present invention may be used to remove the analyte anions or cations or both.

In other embodiments, not shown, the purifier will also remove any interfering neutral compounds in the system eluent. An additional section of neutralized porous resin, preferably of high surface area as disclosed in U.S. Pat. No. 7,329,346 cab be used in these embodiments to purify the eluent of any neutral interfering components.

Figure 2:
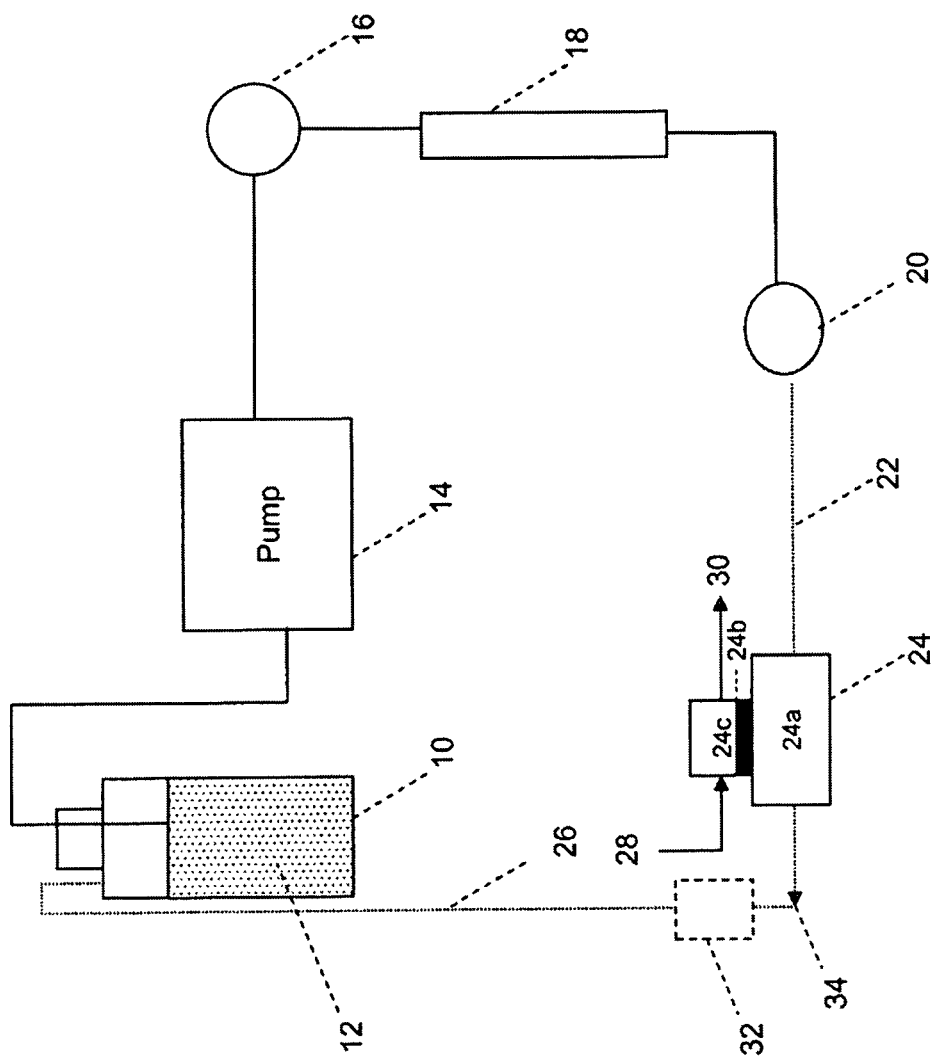

FIG. 2 illustrates a system similar to FIG. 1. Like parts are labeled with like numbers. In FIG. 2, the effluent from detector 20 is routed via conduit 22 to an electrolytic continuously regenerated purifying device 24 in the form of a trap column. Here, the ion exchange removal medium is an ion exchange membrane in a continuous electrolytic device as illustrated in the embodiment of FIG. 2. The sample solution flows through sample stream flow channel 24a on the opposite side of ion exchange membrane 24b from a flowing stream of liquid in regenerant channel 24c. A pair of electrodes, not shown, are in electrical communication with channels 24a and 24c, respectively, and are connected to a power source. The construction and operation of this continuous electrolytic device are similar to a conventional continuous electrical suppressor such as illustrated in U.S. Pat. No. 7,329,346, except that, in the present invention, the purifier is downstream of the detector, i.e., it is located between the detector and the chromatography column.

The function of purifier 24 is to electrolytically and continuously remove the analyte cations or anions and replace them with hydronium or hydroxide ions, respectively. For example for cation analysis, the cation sample ions can be removed by the Dionex CR-CTC column purifier device and replaced with hydronium ions. The advantage of this approach over the packed bed approach of FIG. 1 is that there is no need for periodic regeneration (i.e., it operates continuously). In one embodiment, an optional degasser 32 can be used to remove electrolytic gas generated by the purifier. It should be noted that the CR-TC could be designed with electrodes that are not in the eluent pathway and with this mode the degasser can be omitted. In one embodiment, the electrolytic continuously regenerated purifier device and degas device and their operation are illustrated in US Application Publication No. 2003/0127392, incorporated by reference. By way of example, the CR-ATC device designed for anions will remove anionic contaminants and analyte from the eluent stream and replace this with hydroxide. In some instances the CR-ATC may remove the eluent anion which could alter the eluent concentration. Therefore, under these conditions, a packed bed of ion exchange resin may be used in the eluent anion form since this would preserve the eluent composition.

An external DI water stream may be used to flow through the regenerant channel 24c, e.g. of the CR-TC as depicted in FIG. 2. This stream may be routed to waste at 30 or recycled for a short duration back to the source 28 via a reservoir. It should be noted that electrolytic membrane based devices that replace the analyte ion with hydronium or hydroxide ions, as the case may be, could be used in this embodiment for purifying the eluent without altering the original eluent composition. Suitable electrolytic membrane devices can be constructed similar to a commercial suppressor device as described in U.S. Pat. No. 4,999,098, incorporated by reference.

Typical chromatography developing electrolytes in aqueous eluents suitable for SCIC anion analysis are carboxylic acids and sulfonic acids and salts thereof such as sodium or potassium salts of benzoic acid, phthalic acid, sulfobenzoic acid, citric acid, phenolic acid. P-hydroxybenzoic acid adjusted to pH 8.5 is a suitable eluent for eluting monovalent and divalent ions. Basic electrolytes in eluents such as sodium hydroxide, potassium hydroxide, pyridine, amines and diamines could also be used alone or in combination with the organic acids listed above. Similarly typical electrolytes in eluents for SCIC for cation analysis are acids such as nitric acid, methane sulfonic acid, tartaric acid with added dipyridine carboxylic acid, ammonium carbonate and phenylene diamine.

During the recycle operation, the decision to replenish the eluent may be made by observing the chromatographic performance and evaluating the acceptance criteria. The SCIC system is operated following a calibration therefore small changes in retention time and peak response due to a change in background can be easily calibrated. A preferred time to replenish the eluent may be determined by observing the peak efficiency of the separated components. For example when the efficiency drops by 50% or more and preferably by about 30% and most preferably by about 10%, the eluent can be replenished.

The devices of the present invention could be operated under a variety of flow rate conditions. Preferable flow rates are in the 0 to 2 ml/min and more preferably the flow rate is proportional to the internal diameter of the chromatography column. For example it is well accepted that standard bore columns are typically operated in the 0.5 to 2 ml/min and micro bore columns are operated in the 0.2 to 0.5 ml/min and so on and so forth.

In order to further illustrate the present invention, the following non-limiting examples are provided.

Example 1

A Dionex ICS 3000 system was used for this work for cation analysis. An eluent comprising 4 mM Tartaric acid with 0.75 mM 2,6-pyridine dicarboxylic acid (PDCA) was used for this work at a starting volume of 500 mL. A cation exchange column (2×250 mm) was used as the analytical column in this work at a flow rate of 0.25 ml/min. A CR-CTC continuously regenerated cation trap column was used to purify the eluent after detection as shown in FIG. 2. The CR-CTC was powered with an external 12 V constant voltage power supply. A degas module from Dionex used in its EG system was used to remove the electrolytically generated oxygen gas and the purified eluent was returned back into the eluent reservoir 10. (It is possible to bypass the degasser with suitable design of the CR-CTC. Another possibility is to simply bubble the electrolytic gas out of the solution in the reservoir and evacuate the gas into the ambient environment.)

Figure 3A:
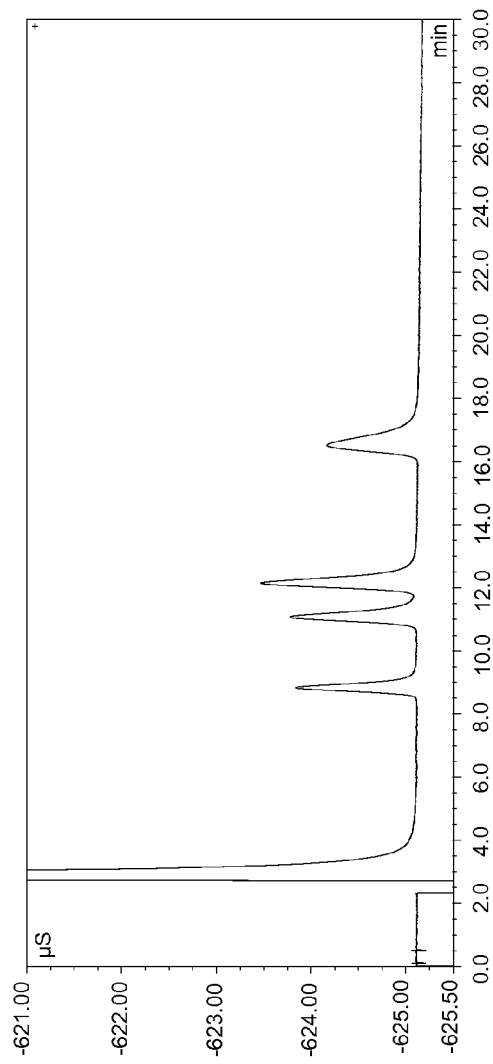
FIGS. 3*a* and 3*b*, 4*a* and 4*b* are chromatograms of experimental results according to the invention.
Figure 3B:
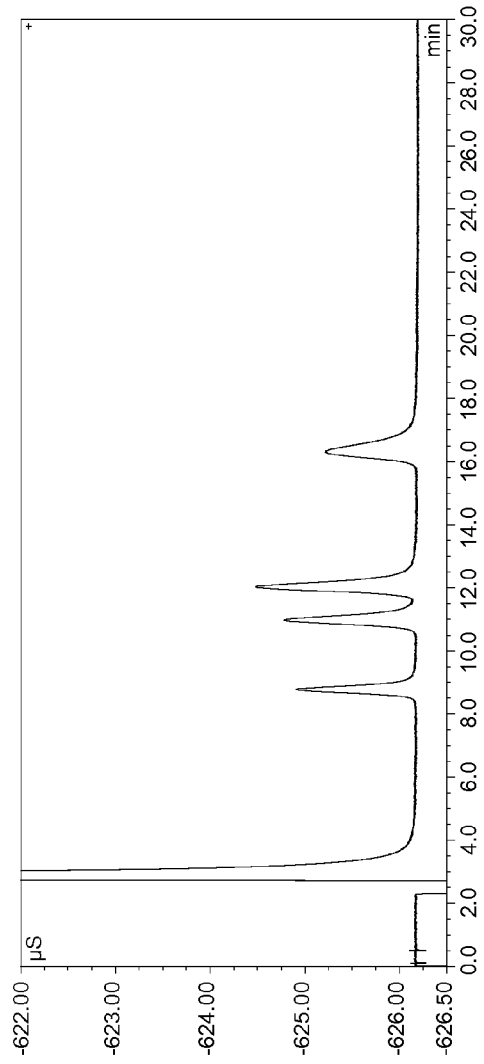

The CR-CTC regenerant channel was continuously swept with deionized water to help remove any anionic impurities from the eluent. This stream was recycled using a 1 L reservoir of DI water filled with 500 mL of DI water and was replaced after 2 weeks of operation. A test mixture comprising of four monovalent cations (lithium, sodium, ammonium and potassium) was used in this work in the mg/L regime. Samples were intermittently injected over a period of 30 days while the instrument was continuously recycling the eluent. Excellent resolution of the four monovalent cations was achieved as shown in FIG. 3A. FIG. 3B shows the separation after 30 days of continuous running and showed very little change in performance.

Example 2

The performance parameters from Example 1 are compared below and show very little change in retention time, peak response and efficiency after one month of continuous operation. Overall excellent performance can be inferred from the recycle single column ion chromatograph of the present invention. The total volume usage of the eluent was 0.5 L in the recycle mode versus 10.8 L in the standard mode of operation. Additionally the disposal of waste was also significantly reduced.

It is apparent from the examples that the recycle system of the present invention preserves the chromatographic performance while recycling the eluent and generating very little waste.

|  |  | Upon Installation | | | After one month of continuous operation | | |
| --- | --- | --- | --- | --- | --- | --- | --- |
| No | Peak | Retention time Minutes | Pk. Area uS * min/cm | Efficiency Plates | Retention time Minutes | Pk. Area uS * min/cm | Efficiency Plates |
| 1 | Lithium | 8.84 | 0.366 | 6538 | 8.78 | 0.365 | 7115 |
| 2 | Sodium | 11.07 | 0.459 | 6952 | 10.977 | 0.459 | 7550 |
| 3 | Ammonium | 12.147 | 0.624 | 7162 | 12.023 | 0.624 | 7797 |
| 4 | Potassium | 16.517 | 0.558 | 5473 | 16.297 | 0.559 | 6303 |

Example 3

Figure 4A:
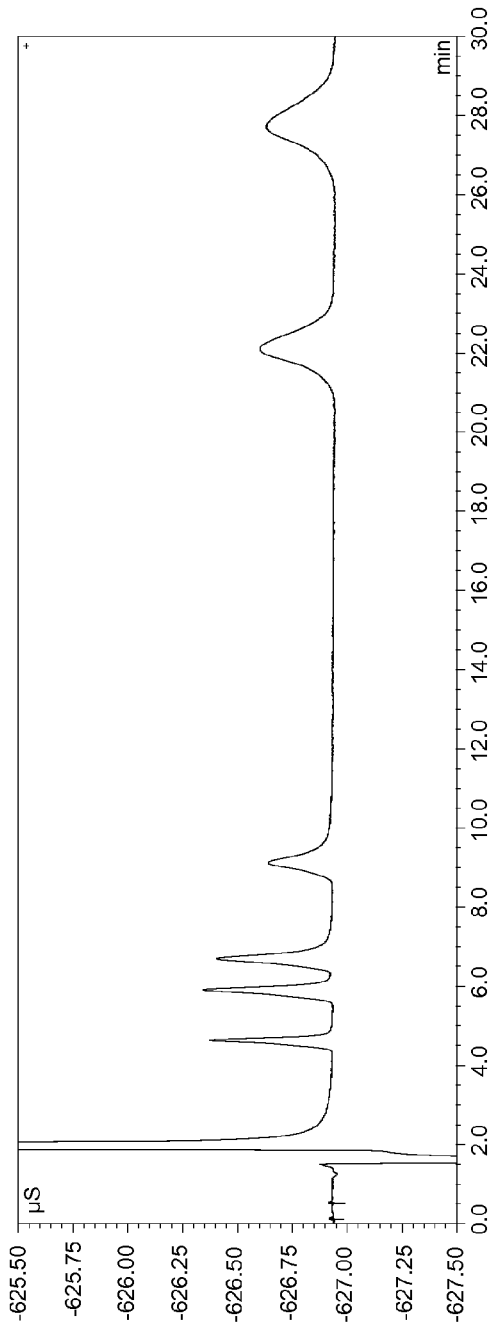
Figure 4B:
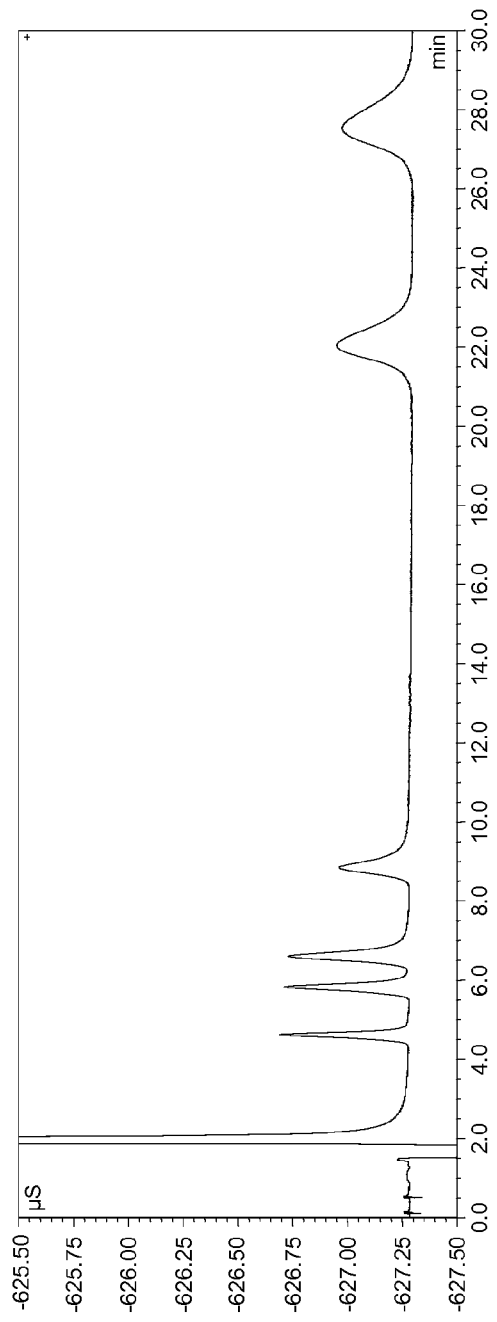

In this example, a single column from Metrohm Instruments called Metrosep C2 column (4×150 mm) was used in this work at a flow rate of 1 ml/min. All other conditions remained similar to Example 1. A cation test mix comprising of 6 cations was analyzed in this work. The system was run continuously with continuous injections. FIGS. 4a and 4b compare the performance of the separation before and after 1 week of continuous operation. Excellent reproducibility could be inferred from this figure. The eluent consumption remained at 0.5 L in the recycle mode versus 10.8 L in the standard single column mode of operation. Since the flow rate was 1 ml/min significant savings could be inferred from above within one week of operation.

Example 4

The performance parameters are compared below and show very little change in retention time, peak response and efficiency after 7 days of continuous use. Overall excellent performance can be inferred from the recycle single column ion chromatograph of the present invention.

|  |  | Upon Installation | | | After 1 week of continuous operation | | |
| --- | --- | --- | --- | --- | --- | --- | --- |
| No. | Peak | Retention time Minutes | Pk. Area uS * min/cm | Efficiency Plates | Retention time Minutes | Pk. Area uS * min/cm | Efficiency Plates |
| 1 | Lithium | 4.627 | 0.1011 | 5680 | 4.637 | 0.0988 | 5562 |
| 2 | Sodium | 5.837 | 0.1239 | 5256 | 5.907 | 0.1363 | 4980 |
| 3 | Ammonium | 6.61 | 0.1602 | 4105 | 6.7 | 0.1583 | 4282 |
| 4 | Potassium | 8.837 | 0.1395 | 3262 | 9.103 | 0.1356 | 3516 |
| 5 | Calcium | 22.047 | 0.3363 | 3560 | 22.087 | 0.3267 | 3783 |
| 6 | Magnesium | 27.56 | 0.3915 | 3347 | 27.74 | 0.3881 | 3554 |

Example 5

The IC recycle system was setup for anion analysis. A 4×250 mm AS11 column from Dionex corporation was used in this work with an eluent comprising of Pthalic acid and Tris base. A 9×50 mm ATC-HC trap column was used as the purifier in this work. An ATC-HC trap column was used for this application which was converted to the phthalate form by pumping in eluent. A standard comprising of 5 anions was analyzed. The system was run continuously for a week. The RSD in retention time and peak area for chloride was monitored and was 0.19% and 1.6% respectively for n=200 runs. This demonstrated excellent performance of the system for single column ion chromatography analysis.

What is claimed is:

1. An ion chromatography apparatus comprising,
 (a) a chromatographic column, having an inlet and an outlet, including ion exchange separation medium having exchangeable ions of one charge, positive or negative, for separating analyte ions of the same charge as said exchangeable ions, said chromatographic column not being associated with electrodes for passing an electric current through said separation medium,
 (b) a source of an aqueous eluent liquid stream in fluid communication with said chromatographic column inlet,
 (c) a detector, including an inlet and an outlet, for detecting analyte ions in a sample downstream from said chromatographic column outlet, said detector inlet being in fluid communication with said chromatographic column outlet,
 (d) a recycle line providing fluid communication between said detector and said chromatographic column inlet,
 (e) an electrolytic purifying device comprising a regenerant channel separated from a sample stream flow channel by an ion exchange removal membrane, said purifying device being capable of continuous regeneration by applying an electric field across said ion exchange removal membrane disposed along said recycle line, said ion exchange removal membrane including exchangeable ions of the same charge as said separation medium exchangeable ions, said sample stream flow channel being in fluid communication with said detector outlet, said apparatus not including a suppressor disposed between said chromatographic column outlet and said detector, and
 (f) an external water source being in fluid communication with said regenerant channel but not in fluid communication with said recycle line.

2. The apparatus of claim 1 in which said detector is a conductivity detector.

3. The apparatus of claim 1 further comprising a pair of electrodes disposed to pass electric current through said ion exchange removal membrane.

4. The ion chromatography apparatus of claim 1 in which said purifying device is for removal of sample analyte ions in said eluent liquid stream, said purifying device further comprising eluent liquid from said eluent liquid stream in contact with said ion exchange removal membrane.

* * * * *